United States Patent
Christman et al.

(10) Patent No.: US 10,611,880 B2
(45) Date of Patent: Apr. 7, 2020

(54) OXIME CROSS-LINKED BIOCOMPATIBLE POLYMER HYDROGELS AND METHODS OF USE THEREOF

(71) Applicant: The Regents of the University of California, Oakland, CA (US)

(72) Inventors: Karen Christman, San Diego, CA (US); Gregory Grover, Carlsbad, CA (US); Michael Madani, La Jolla, CA (US); Masaki Fujita, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 169 days.

(21) Appl. No.: 15/534,269

(22) PCT Filed: Dec. 9, 2015

(86) PCT No.: PCT/US2015/064749
§ 371 (c)(1),
(2) Date: Jun. 8, 2017

(87) PCT Pub. No.: WO2016/094535
PCT Pub. Date: Jun. 16, 2016

(65) Prior Publication Data
US 2017/0362380 A1    Dec. 21, 2017

Related U.S. Application Data

(60) Provisional application No. 62/089,576, filed on Dec. 9, 2014.

(51) Int. Cl.
*C08G 65/48* (2006.01)
*A61L 31/14* (2006.01)
(Continued)

(52) U.S. Cl.
CPC .......... *C08G 65/48* (2013.01); *A61L 24/0031* (2013.01); *A61L 31/145* (2013.01);
(Continued)

(58) Field of Classification Search
CPC ...................................................... C08G 65/48
See application file for complete search history.

(56) References Cited

U.S. PATENT DOCUMENTS

| 2003/0060446 A1* | 3/2003 | Wang | C07H 17/02 514/54 |
|---|---|---|---|
| 2010/0112063 A1 | 5/2010 | Figuly et al. | |

(Continued)

FOREIGN PATENT DOCUMENTS

WO    2014/039245 A1    3/2014

OTHER PUBLICATIONS

PCT International Search Report and Written Opinion for PCT Application No. PCT/US2015/064749 dated Feb. 23, 2016 (7 pages).

*Primary Examiner* — Michael F Pepitone
(74) *Attorney, Agent, or Firm* — Eversheds Sutherland (US) LLP (57) ABSTRACT

Methods and hydrogels for preventing or reducing cellular adhesion and protein adsorption to a tissue (e.g. cardiac tissue) are disclosed. The hydrogels generally include at least two component polymers, a first polymer including an aminooxy group and a second polymer including a reactive oxo group, that are cross-linked by oxime bonds. The hydrogels are suitable for binding to and coating a tissue or cell. The hydrogels operate to reduce cellular adhesions and protein adsorption to the tissue or cell.

26 Claims, 7 Drawing Sheets

(51) Int. Cl.
*A61L 24/00* (2006.01)
*C08J 3/24* (2006.01)
*C08J 3/075* (2006.01)
*C08F 16/06* (2006.01)
C08B 37/02 (2006.01)
C08B 37/08 (2006.01)

(52) U.S. Cl.
CPC ............ *C08F 16/06* (2013.01); *C08J 3/075* (2013.01); *C08J 3/246* (2013.01); *C08B 37/0021* (2013.01); *C08B 37/0072* (2013.01); *C08G 2650/50* (2013.01); *C08J 2300/206* (2013.01); *C08J 2371/02* (2013.01); *C08J 2400/206* (2013.01); *C08J 2471/02* (2013.01)

(56) References Cited

U.S. PATENT DOCUMENTS

| | | |
|---|---|---|
| 2010/0291224 A1 | 11/2010 | Tong et al. |
| 2011/0008444 A1* | 1/2011 | Bergman ............ A61L 24/0015 424/488 |
| 2013/0280783 A1 | 10/2013 | Culbertson et al. |

* cited by examiner

Gelation time (seconds)
100mg/mL, ald:AO=1:1

|  |  | AO | |
|---|---|---|---|
|  |  | 8PEG(10K) | 8PEG(5K) |
| ald | 8PEG(10K) | 2 | 4 |
|  | 8PEG(5K) | 4 | 2 |
|  | PEG-PVA | 5 | 5 |

FIGURE 15A

Gelation time (seconds)
100mg/mL, ald:AO=3:1

|  |  | AO | |
|---|---|---|---|
|  |  | 8PEG(10K) | 8PEG(5K) |
| ald | 8PEG(10K) | 2 | 4 |
|  | 8PEG(5K) | 120 | 2 |
|  | PEG-PVA | 30 | 4 |

FIGURE 15B

Gelation time (seconds)
100mg/mL, ald:AO=1:3

|  |  | AO | |
|---|---|---|---|
|  |  | 8PEG(10K) | 8PEG(5K) |
| ald | 8PEG(10K) | 20 | 30 |
|  | 8PEG(5K) | 210 | 300 |
|  | PEG-PVA | NA | NA |

FIGURE 15C

Gelation time (seconds)
50mg/mL, ald:AO=1:1

|  |  | AO | |
|---|---|---|---|
|  |  | 8PEG(10K) | 8PEG(5K) |
| ald | 8PEG(10K) | 30 | 30 |
|  | 8PEG(5K) | >3600 | 180 |
|  | PEG-PVA | NA | NA |

FIGURE 15D

OXIME CROSS-LINKED BIOCOMPATIBLE POLYMER HYDROGELS AND METHODS OF USE THEREOF

CROSS REFERENCE TO RELATED APPLICATIONS

This application claims the priority benefit of PCT/US2015/064749 filed on Dec. 9, 2015 which claims priority benefit of U.S. provisional patent application Ser. No. 62/089,576, filed Dec. 9, 2014. The entire contents of which are hereby incorporated by reference herein.

FIELD OF THE INVENTION

The present disclosure relates generally to hydrogels and methods of use thereof and, more particularly, oxime cross-linked biocompatible polymer hydrogels.

BACKGROUND OF THE INVENTION

As a result of the healing process that follows surgery, complications frequently arise due to the natural tendency of the body to form adhesions. Postsurgical adhesions negatively impact patient comfort and organ function.[3-5] Post-surgical adhesions are particularly problematic for cardiac surgery patients. Many patients that have cardiac surgery, especially pediatric patients, must undergo reoperative procedures during their lifetime.[6-8] The presence of postsurgical cardiac adhesions increases the difficulty and risks of the reoperative procedure due to increased surgery times and potential hemorrhaging upon gaining re-access to the heart.[8]

Two main approaches exist for reducing or attempting to prevent cardiac adhesions: pharmacological therapy and physical barriers. Drugs that prevent or reverse adhesion processes disrupt biochemical pathways of inflammation and fibrin deposition (see e.g., WO 2013135647 A1). Unfortunately, these processes are also vital for wound healing. Achieving adequate drug concentration at the site of action, especially for ischemic tissues, is also challenging.

A more viable approach is the use of a physical barrier after surgery to prevent fusion of the heart to surrounding tissues. The barriers can be either preformed membranes (see e.g., US 20120088832 A1, CA 2513640 C, and WO 2013032201 A2) or injectable hydrogels (fast gelling liquids) (see e.g., EP 1967220 A2, EP 2470223 A2 and U.S. Pat. No. 5,874,500 A). Preformed anti-adhesive materials need to be cut before application to the tissue, and must be sutured into place to prevent slippage. Injectable hydrogels allow the freedom of applying material where needed by "painting" or spraying the precursor components and are capable of quickly forming a protective gel over the surface of the tissue. Therefore, a promising method to prevent postsurgical adhesions is to coat the tissue with a fast gelling polymer to prevent the susceptible tissue from adhering to other nearby tissue organs.[3]

Materials that bind to tissues are widely used in clinical procedures; including abdominal, brain, spine, and cardiac surgeries. These materials are used to achieve homeostasis, seal tissues, deliver exogenous substances locally, or prevent postsurgical adhesions. The safety and efficacy of these materials is directly impacted by the purity of the components and mode of material formation.[1,2] For synthetic materials, the cross-linking chemistry and subsequent degradation products can dramatically impact the biocompatibility of the material.[1] There are, however, only a limited number of materials that prevent postsurgical adhesions in a clinical setting. Further, while a variety of different materials have been investigated in animals and humans, no materials to date, have been capable of preventing adhesion formation post-cardiac surgery.

The mechanism of material adherence to tissue can be divided into two modes, non-covalent and covalent. Non-covalent materials include collagen, fibrin, and gelatin as well as ionic and thermoresponsive polymers. While these materials generally exhibit good biocompatibility, they are rapidly degraded or removed from the tissue surface in vivo due to the non-covalent association. Additionally, the protein-based materials contain ligands that promote cellular attachment, which is not ideal for preventing postsurgical adhesions that are the result of inflammation.[3,9]

Covalent attachment can be achieved through two different approaches. One approach uses radical polymerization or anionic polymerization (cyanoacrylates). However, due to the polymerizable functional groups these systems have exhibited toxicity in vivo.[1,10] The other covalent approach relies on reaction with nucleophilic functional groups present on the tissue surface by using epoxides, activated carboxylic acids, or aldehydes. This approach is attractive since the materials can be synthesized with a desired number of functional groups and molecular weights to tune tissue reactivity, gelation times, and facilitate clearance from the body upon degradation.[1]

From a chemistry perspective, adhesion prevention is challenging, especially in a cardiac surgery setting. The material should be easily applied, gel rapidly (<5 min) on the wet tissue surface, remain on the tissue for at least 2 weeks to overcome the initial inflammatory response post-surgery, exhibit minimal swelling (to not impede cardiac function), and be biocompatible. This means that the pre-gel materials must be capable of reacting quickly and efficiently with themselves as well as with tissue, and the cross-linking functional groups must be biocompatible. Once gelled, the material must prevent cellular adhesion to prevent fibrin deposition from infiltrating cells, since this leads to adhesions.[3]

Oxime chemistry has been successfully used in a variety of in vitro and in vivo applications,[11] and PEG-coated surfaces have shown to minimize protein adsorption[12] and cellular adhesion.[13] It has been demonstrated that oxime chemistry is biocompatible, chemospecific, and bioorthogonal.[11,14]

Therefore, what are needed are improved methods and compositions for use as an anti-adhesion barrier. It would be desirable to employ a new chemistry that results in rapid forming hydrogels capable of adhering to tissue surfaces. The present invention addresses these and other related needs in the art.

SUMMARY OF THE INVENTION

In some embodiments, an oxime cross-linked biocompatible hydrogel is provided, which includes: a first polymer comprising an aminooxy group selected from a hydroxyl amine and an alkoxy amine polymerized to a second polymer comprising a reactive oxo group, wherein the hydrogel has a surface comprising a surface oxo group that reversibly binds an amine group on a living tissue surface to form an imine. In some embodiments, the reactive oxo group and the surface oxo group are ketones. In some embodiments, the reactive oxo group and the surface oxo group are aldehydes. In some embodiments, the first polymer and the second polymer are each selected from the group consisting of poly(ethylene glycol), multi-arm poly(ethylene glycol), hyaluronic acid, alginate, dextran, carboxymethylcellulose, cellulose, poly(vinyl alcohol), or combinations thereof. In some embodiments, the first polymer comprises eight-armed aminooxy poly(ethylene glycol) and the second polymer comprises eight-armed oxo poly(ethylene glycol). In some embodiments, the first polymer comprises eight-armed aminooxy poly(ethylene glycol) and the second polymer comprises aldehyde poly(ethylene glycol)-poly(vinyl alcohol). In some embodiments, the hydrogel comprises approximately between 25 and 200 mg/mL of the first polymer and the second polymer. In some embodiments, the hydrogel has a storage modulus of about less than 1 kPa. In some embodiments, the hydrogel swells to less than about 150% by volume when hydrated. In some embodiments, the hydrogel further comprises a bioactive agent.

In some embodiments, a method of administering an oxime cross-linked bioadhesive hydrogel to a tissue for use as an in-situ anti-adhesion barrier is provided, the method comprising: administering to a living tissue of an individual an effective amount of a combination of a first polymer comprising an aminooxy group selected from a hydroxyl amine and an alkoxy amine, and a second polymer comprising a reactive oxo group, wherein the first polymer and second polymer are mixed and react to form an oxime cross-linked biocompatible hydrogel proximate to the tissue, wherein the hydrogel has a surface comprising a surface oxo group, and wherein the surface oxo group reversibly binds a surface amine on the tissue to form an imine. In some embodiments, the tissue is cardiac tissue or another tissue found in the individual's thoracic cavity. In some embodiments, the oxime cross-linked biocompatible hydrogel is formed in about 5 minutes or less. In some embodiments, the first polymer and the second polymer are administered by spraying, dripping, or painting the first polymer and the second polymer directly onto the tissue. In some embodiments, the hydrogel is capable of adhering to the tissue for about two or more weeks. In some embodiments, the hydrogel reduces cellular adhesion and protein adsorption to the tissue. In some embodiments, the method further comprises reversing hydrogel cross-linking by administering a free aminooxy group selected from a hydroxyl amine and an alkoxy amine, or a reactive oxo group.

BRIEF DESCRIPTION OF THE DRAWINGS

Those of skill in the art will understand that the drawings, described below, are for illustrative purposes only. The drawings are not intended to limit the scope of the present teachings in any way.

FIGS. 5A-5B. Formation of fast-gelling PEG hydrogels.

FIGS. 6A-6B.

FIGS. 13A-13B.

FIGS. 15A-15D. Gelation rate between ald-polymer such as PEG (10,000 g/mole), PEG (5,000 g/mole) and PEG-PVA, and AO-polymer such as PEG (10,000 g/mole) and PEG (5,000 g/mole).

DETAILED DESCRIPTION OF THE INVENTION

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

It is understood that aspects and embodiments of the invention described herein include "consisting" and/or "consisting essentially of" aspects and embodiments.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The term "hydrogel" refers to a water-swellable polymeric matrix comprising a network of macromolecules held together by covalent cross-links that can absorb water to form an elastic gel.

The term "cross-link" refers to a bond or chain of atoms attached between and linking two different polymer chains.

The term "PEG" as used herein refers to poly(ethylene glycol).

The term "multi-arm PEG" refers to a branched poly(ethylene glycol).

The term "PVA" as used herein refers to poly(vinyl alcohol).

The term "AO" refers to an aminooxy group.

The term "RO" refers to a reactive oxo group.

The term "AO-PEG" refers to a poly(ethylene glycol) that is derivatized (i.e. chemically modified) to contain an aminooxy group.

The term "RO-PEG" refers to a poly(ethylene glycol) that is derivatized (i.e. chemically modified) to contain a reactive oxo group.

The term "RO-PEG-PVA" refers to a poly(ethylene glycol)-poly(vinyl alcohol) copolymer that is derivatized (i.e. chemically modified) to contain a reactive oxo group.

The term "ald-PEG" refers to a poly(ethylene glycol) that is derivatized (i.e., chemically modified) to contain an aldehyde group.

The term "ald-PEG-PVA" refers to a poly(ethylene glycol)-poly(vinyl alcohol) copolymer that is derivatized (i.e. chemically modified) to contain an aldehyde group.

A "branched" polymer refers to a polymer having one or more branch points ("arms"), and includes star, dendritic, comb, and hyperbranched polymers. In some embodiments, branched polymers can have between 3 and 100 arms.

A "star" polymer refers to a polymer having a central branch point, which may be a single atom or a chemical group, from which arms emanate.

It should be recognized that branched or multi-arm polymers can be a somewhat heterogeneous mixture having a distribution of species with different numbers of arms. When a multi-arm polymer has a distribution of species having different numbers of arms, it can be referred to based on the average number of arms in the distribution. For example, in one embodiment, a hydrogel precursor is an 8-arm star PEG (each arm being terminated by aminooxy group) which comprises a mixture of multi-arm star PEG, some having less than and some having more than 8 arms; however, the multi-arm star PEG in the mixture have an average of 8 arms. Therefore, the terms "8-arm", "6-arm", "4-arm", "3-arm", and the like, as used herein to refer to multi-arm polymers, should be construed as referring to a homogeneous mixture or a heterogeneous mixture having a distribution of species with different numbers of arms, in which case the number of arms recited refers to the average number of arms in the mixture.

The term "tissue" refers to any biological tissue in individual humans or animals.

The term "prevent" is meant to indicate postponing, suppressing, or reducing the risk of developing or recurrence of a disease, disease symptom, and/or medical condition.

B. Oxime Cross-Linked Hydrogels

Disclosed herein are oxime cross-linked hydrogel tissue adhesives formed by reacting a first polymer (i.e. a first precursor) comprising a reactive oxo group with a second polymer (i.e. a second precursor) comprising an aminooxy group. The hydrogel may be useful as a tissue adhesive or sealant for medical applications including, but not limited to, prevention of undesired post-surgical tissue adhesions. The hydrogel can act as a barrier that isolates organs or tissue from each other for a predetermined period, depending on the absorption and/or degradation profile of the hydrogel. In some embodiments, the tissue is cardiac tissue or another tissue in the thoracic cavity.

Hydrogel Precursors and Hydrogels

In general, at least two types of hydrogel precursors are provided. A first hydrogel precursor comprises a polymer terminated with an aminooxy group. Various aminooxy groups suitable for use in the present invention are well known to those of ordinary skill in the art. Exemplary aminooxy groups include hydroxyl amines, alkoxyl amines, and the like. A second hydrogel precursor comprises a polymer terminated with a reactive oxo group. Various reactive oxo groups suitable for use in the present invention are well known to those of ordinary skill in the art. Exemplary reactive oxo groups include ketones, aldehydes, and the like.

Polymers suitable for use as hydrogel precursors can include poly(ethylene glycol), branched or multi-arm poly(ethylene glycol), hyaluronic acid, alginate, dextran, carboxymethylcellulose, cellulose, poly(vinyl alcohol), and their copolymers. In some embodiments, hydrogel precursors comprise a multi-arm polymer. In some embodiments, hydrogel precurusors comprise a branched polymer. In some embodiments, hydrogel precursors comprise a star polymer. Polymers suitable for use as hydrogel precursors are either available commercially or may be prepared using methods known in the art. In some embodiments, the polymers used as hydrogel precursors have a molecular weight of about 1,000 g/mol to about 50,000 g/mol.

In some embodiments, hydrogel precursors comprise a multi-arm poly(ethylene glycol) having 3, 4, 6, or 8 arms terminated with aminooxy groups (e.g. hydroxyl amines, alkoxyl amines, and the like). In some embodiments, a hydrogel precursor is an eight-arm poly(ethylene glycol) having eight arms terminated by aminooxy groups (e.g. hydroxyl amines, alkoxyl amines, and the like). In some embodiments, the multi-arm poly(ethylene glycol) having 3, 4, 6, or 8 arms terminated with aminooxy groups (e.g. hydroxyl amines, alkoxyl amines, and the like) has a molecular weight of about 10,000 g/mol or less or 5,000 g/mol or less.

In some embodiments, hydrogel precursors comprise a multi-arm poly(ethylene glycol) having 3, 4, 6, or 8 arms terminated with reactive oxo groups (e.g. ketones, aldehydes, and the like). In some embodiments, a hydrogel precursor is an eight-arm poly(ethylene glycol) having eight arms terminated by reactive oxo groups (e.g. ketones, aldehydes, and the like). In some embodiments, the multi-arm poly(ethylene glycol) having 3, 4, 6, or 8 arms terminated with reactive oxo groups (e.g. ketones, aldehydes, and the like) has a molecular weight of about 10,000 g/mol or less or 5,000 g/mol or less.

In some embodiments, hydrogel precursors comprise a multi-arm poly(ethylene glycol)-poly(vinyl alcohol) copolymer having 3, 4, 6, or 8 arms terminated with reactive oxo groups (e.g. ketones, aldehydes, and the like). In some embodiments, a hydrogel precursor is an eight-arm poly(ethylene glycol)-poly(vinyl alcohol) copolymer having eight arms terminated by reactive oxo groups (e.g. ketones, aldehydes, and the like). In some embodiments, the multi-arm poly(ethylene glycol)-poly(vinyl alcohol) copolymer having 3, 4, 6, or 8 arms terminated with reactive oxo groups (e.g. ketones, aldehydes, and the like) has a molecular weight of about 50,000 g/mol or less, 10,000 g/mol or less, or 5,000 g/mol or less. In some embodiments, hydrogel precursors comprise a branched poly(ethylene glycol)-poly(vinyl alcohol) copolymer terminated with reactive oxo groups (e.g. ketones, aldehydes, and the like). In some embodiments, the branched poly(ethylene glycol)-poly(vinyl alcohol) copolymer terminated with reactive oxo groups (e.g. ketones, aldehydes, and the like) has a molecular weight of about 50,000 g/mol or less, 10,000 g/mol or less, or 5,000 g/mol or less.

The oxime cross-linked hydrogels disclosed herein can swell minimally after deposition. Swelling of a hydrogel relates to its change (or ratio) in volume between the time of its formation when cross-linking is effectively complete and a time after at which point the hydrogel may be reasonably assumed to have achieved its equilibrium swelling state at room temperature. In some embodiments, the hydrogel may achieve an equilibrium swelling state in about 24 hours or less. In some embodiments, the hydrogel volume increases no more than about 0% to about 10% or to about 50% upon exposure to a physiological solution relative to a volume of the hydrogel at the time of formation. In some embodiments, the hydrogel has less than a 20%, 30%, 40%, 50%, 60%, 70%, 75%, 80%, 85%, 90%, 95%, 100%, 110%, 112%, 115%, 120%, 130%, 140%, 150%, or 160% increase in volume when swollen. In some embodiments, cross-linking is effectively complete within no more than about ten minutes. In some embodiments, the hydrogel gels (cross-linking is effectively complete) in about less than 30 seconds, 1 minute, 1.5 minutes, 2 minutes, 2.5 minutes, 3.0 minutes, 3.5 minutes, 4.0 minutes, 4.5 minutes, 5 minutes, or 10 minutes.

A hydrogel formed in a location where it is constrained is not necessarily a low-swelling hydrogel. For instance, a swellable hydrogel created in a body may be constrained from swelling by its surroundings but nonetheless may be a highly swellable hydrogel as evidenced by measurements of its swelling when unconstrained.

In some embodiments, the hydrogel comprises between about 25 mg/mL polymer and about 200 mg/mL polymer.

In some embodiments, the hydrogel has a storage modulus of less than 1 kPA, 2 kPA, 3 kPA, 4 kPA, 5 kPA, or 10 kPA.

In some embodiments, the hydrogel resorbs and/or degrades over a period of time. In some embodiments, the hydrogel takes longer than 5 days, 1 week, or 2 weeks to resorb and/or degrade. In some embodiments, the hydrogel takes less than 1, 2, or 3 months to resorb and/or degrade.

In some embodiments, the polymer precursors and/or hydrogel are biocompatible, biodegradable, and/or substantially water soluble.

In some embodiments, the hydrogel cross-linking can be reversed. In some embodiments, hydrogel cross-linking is reversed with the addition of free aminooxy groups (e.g. hydroxyl amines and alkoxy amines) or free reactive oxo groups (e.g. ketones, aldehydes, and the like).

In some embodiments, the polymer precursors and/or hydrogel further comprises a bioactive agent or an antimicrobial. A bioactive agent can include any drug, pharmaceutical compound, or molecule (e.g. small molecule, protein, peptide, RNA fragments, nucleic acid, inorganic and organic biologically active compounds, etc.) having a therapeutic effect. Suitable bioactive agents are well known in the art (see e.g. the United States Pharmacopeia (USP), Physician's Desk Reference, and the like). In some embodiments, the bioactive agent may be an anti-inflammatory agent and/or a healing promoter.

In some embodiments, the physicochemical properties of the hydrogel including gelation time, gelation rate, lifespan, degradation, mechanical strength and/or water content can be controlled and are tunable based upon the molecular weight of the polymer precursors used, the weight percent of the polymer precursors, the number of cross-linking sites or arms on the polymers, and other parameters known in the art. In some embodiments, increasing the number of cross-linking sites or arms increases the gelation rate. In some embodiments, decreasing the molecular weight of polymers increases the gelation rate. In some embodiments, the hydrogel contains hydrolysable ester linkages that can be manipulated to tune the rate of hydrolysis of the hydrogel post-gelation.

Hydrogel Delivery

The oxime cross-linked hydrogels disclosed herein may be used to form a coating on an anatomical site or tissue of a living organism. In some embodiments, hydrogel precursors are components of aqueous solutions or dispersions. In some embodiments, a first aqueous solution or dispersion comprises a polymer terminated with an aminooxy group and a second aqueous solution or dispersion comprises a polymer terminated with a reactive oxo group. The optimal concentrations of the polymers in the two aqueous solutions or dispersions depends on the intended application, and can be readily determined by one skilled in the art using routine experimentation.

For use on living tissue, in some embodiments, it is preferred that the first aqueous solution or dispersion and the second aqueous solution or dispersion be sterilized to prevent infection. Any suitable sterilization method known in the art that does not degrade the components may be used. Exemplary sterilization methods can include using heat, ethylene oxide sterilization, ultra-violet radiation, or ultra-filtration through a pore membrane.

The aqueous solution(s) or dispersion(s) may further comprise various additives depending on the intended application. The amount of the additive used depends on the particular application and may be readily determined by one skilled in the art using routine experimentation. For example, the aqueous solution(s) or dispersion(s) may comprise one or more additives such as pH modifiers, viscosity modifiers, antimicrobials, colorants, surfactants, and bioactive agents.

The aqueous solution(s) or dispersion(s) may include at least one pH modifier to adjust the pH. Suitable pH modifiers are well known in the art. The pH modifiers may be acidic or basic compounds.

The aqueous solution(s) or dispersion(s) may include at least one viscosity modifier. In some embodiments, the aqueous solution(s) or dispersion(s) include at least one thickening or thinning agent. Suitable thickening or thinning agents are well known in the art.

The aqueous solution(s) or dispersion(s) may include at least one antimicrobial agent. Suitable antimicrobial agents are well known in the art. Examples of antimicrobials that may be suitable include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The aqueous solution(s) or dispersion(s) may include at least one colorant to enhance the visibility of the solution(s) or dispersion(s). Suitable colorants can include, but are not limited to, dyes, pigments, and natural coloring agents.

The aqueous solution(s) or dispersion(s) may include at least one surfactant. Surfactant, as used herein, refers to a compound that lowers the surface tension of water. Suitable surfactants are well known in the art.

The aqueous solution(s) or dispersion(s) may optionally include at least one bioactive agent. A bioactive agent can include any drug, pharmaceutical compound, or molecule (e.g. small molecule, protein, peptide, RNA fragments, nucleic acid, inorganic and organic biologically active compounds, etc.) having a therapeutic effect. Suitable bioactive agents are well known in the art (see e.g. the United States Pharmacopeia (USP), Physician's Desk Reference, and the like). In some embodiments, the bioactive agent may be an anti-inflammatory agent and/or a healing promoter.

The aqueous solution(s) or dispersion(s) may be applied to an anatomical site or tissue of a living organism to form a coating in any number of ways. In some embodiments, once a first aqueous solution or dispersion comprising a polymer terminated with an aminooxy group and a second aqueous solution or dispersion comprising a polymer terminated with a reactive oxo group are applied to a site, they cross-link to form a hydrogel, a process that typically takes about 2 seconds to about 10 minutes.

In some embodiments, two aqueous solutions or dispersions are applied to a site simultaneously or sequentially using any suitable means including, but not limited to, spraying, brushing or painting (e.g. with a cotton swab or brush), dripping, or extrusion using a pipette or a syringe which may be fitted with a hypodermic needle, a nozzle, or tubing to help direct fluid flow. The solutions or dispersions may be applied in any order when applied sequentially. In some embodiments, the solutions or dispersions are further mixed at the site. The further mixing can be done using any suitable means well known in the art such as by using a device such as a cotton swab, a spatula, a brush, or the tip of a pipette or syringe.

In some embodiments, two aqueous solutions or dispersions are mixed before application to a site. The resulting mixture is then applied to the site before the mixture completely cures. The resulting mixture can be applied to a site using any suitable means including, but not limited to, spraying, brushing or painting (e.g. with a cotton swab or brush), dripping, or extrusion using a pipette or a syringe which may be fitted with a hypodermic needle, a nozzle, or tubing to help direct fluid flow.

In some embodiments, two aqueous solutions or dispersions are applied to a site simultaneously where they mix to form a hydrogel.

In some embodiments, two aqueous solutions or dispersions are contained in separate barrels of a double-barrel syringe. In this way the two aqueous solutions or dispersions are applied simultaneously to a site with the syringe. Suitable double-barrel syringe applicators are known in the art.

In some embodiments, two aqueous solutions or dispersions are applied to a site using a spray device. In some embodiments, two aqueous solutions or dispersions are applied to a site simultaneously using a spray device. In some embodiments, the spray device is air-assisted. In some embodiments, the spray device is assisted by compressed air.

Hydrogel Kits

In some embodiments, a kit is provided. In some embodiments, the kit comprises at least one hydrogel precursor having a polymer terminated with an aminooxy group and at least one hydrogel precursor having a polymer terminated with a reactive oxo group. In some embodiments, the kit comprises a first aqueous solution or dispersion having a polymer terminated with an aminooxy group and a second aqueous solution or dispersion having a polymer terminated with a reactive oxo group. Each of the aqueous solutions or dispersions may be contained in any suitable vessel, such as a vial or a syringe barrel.

In some embodiments, the kit comprises at least one hydrogel precursor having a polymer terminated with an aminooxy group in the form of a dried powder and at least one hydrogel precursor having a polymer terminated with a reactive oxo group in the form of a dried powder. The powders may be contained in separate containers or they may be premixed and contained in a single container. The kit may also comprise a buffer solution for hydrating the powders.

C. Examples

In some embodiments, a new approach is provided to prevent postsurgical cardiac adhesions using rapidly forming biocompatible polymer hydrogels (e.g. poly(ethylene glycol) (PEG) and/or poly(vinyl alcohol) polymers or copolymers) cross-linked by oxime bonds that form a protective layer over the epicardium. Oxime bond formation is the Schiff base reaction between an aminooxy group (e.g. hydroxyl amine, alkoxyl amine, etc.) and a reactive oxo group (e.g. ketone, aldehyde, etc.), and is used to both cross-link polymers and attach the hydrogel to free amines on the tissue. In some embodiments, the oxime bonds bind to tissue in vivo. The hydrogels, and methods of use thereof, are suitable for preventing or resisting tissue or cell adhesions or protein adsorption.

In some embodiments, a two component polymeric system is provided that can be easily sprayed, dripped, and/or painted directly onto the heart forming an anti-adhesion layer within seconds to minutes. With this system the degree of swelling and degradation time can be controlled yet not interfere with cardiac function. Since the oxime bond is dynamic, the material can also be easily removed if necessary by addition of free aminooxy groups (e.g. hydroxyl amines, alkoxyl amines, etc.) or reactive oxo groups (e.g. ketones, aldehydes, etc.).

Figure 1:
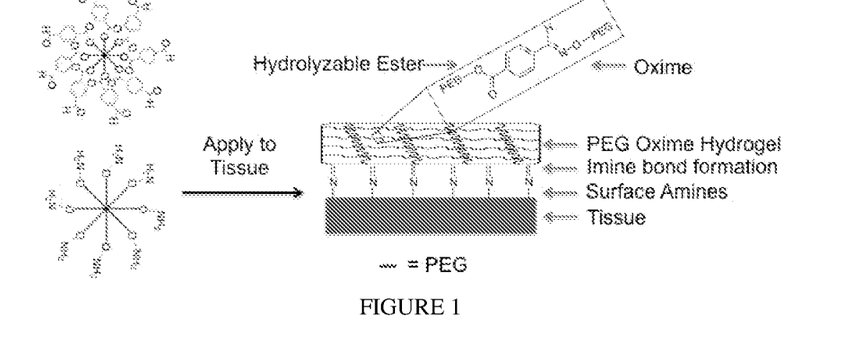
FIG. 1. Formation of oxime cross-linked PEG-hydrogel onto tissue surface.

In some embodiments, the invention provides hydrogels, and methods of use thereof, for preventing or resisting tissue or cell adhesion and/or protein adsorption. In some embodiments, oxime cross-linking chemistry of poly(ethylene glycol) (PEG) was applied to star polymers. Electron deficient aldehyde is capable of reacting with amines on the tissue surface as well as with hydroxylamines to rapidly form a PEG-hydrogel on cardiac tissue (see FIG. 1). This material has the ability to have tunable gelation kinetics, inhibit cellular adhesion, and is capable of adhering to different cardiac tissues for over two weeks.

Figure 2:
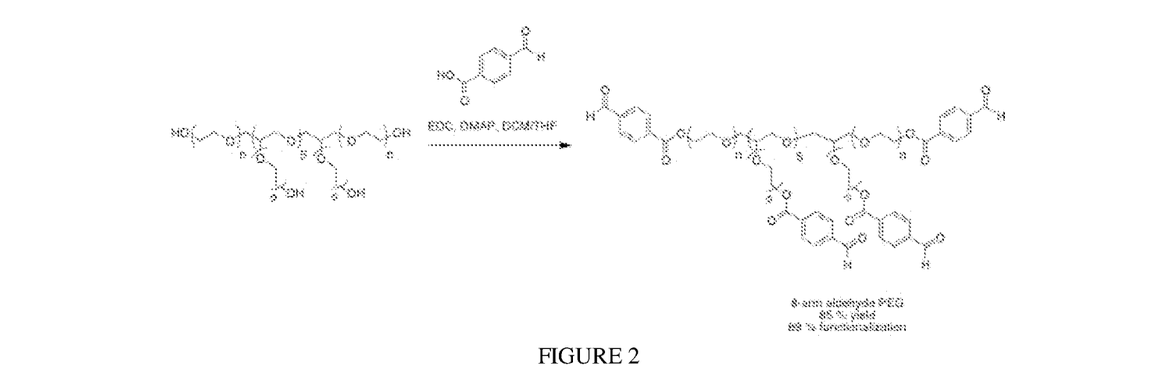
FIG. 2. Synthesis of 8-arm aldehyde-PEG.
Figure 3:
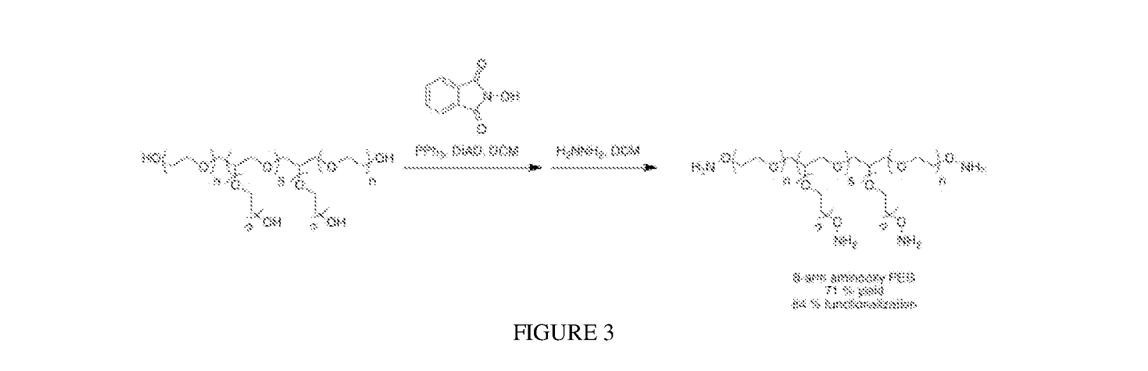
FIG. 3. Synthesis of 8-arm aminooxy PEG.

In some embodiments, materials synthesized via oxime chemistry were used because, since the equilibrium lies far toward the oxime product, these bonds exhibit excellent aqueous stability over imines and hydrazones. Previous work showed this chemistry to form hydrogels for catheter delivery using a 4-arm PEG (20,000 g/mole) esterified with levulinic acid and a 4-arm hydroxylamine PEG (20,000 g/mole). At physiological pH and temperature the 4-arm system exhibited very slow gelation (>2 days).[15] To increase the gelation rate, the electrophilicity of the carbonyl group was increased while a hydrolysable ester was maintained. An 8-arm star PEG (10,000 g/mole and/or 5,000 g/mole) were esterified with 4-carboxylbenzaldehyde (ald-PEG) (see FIG. 2). The 8-arm aminoxy-PEG (AO-PEG) with the 8-arm star PEG (10,000 g/mole and/or 5,000 g/mole) were synthesized via Mitsunobu with N-hydroxyphthalimide followed by deprotection with hydrazine (see FIG. 3).[14, 15]

Figure 4:
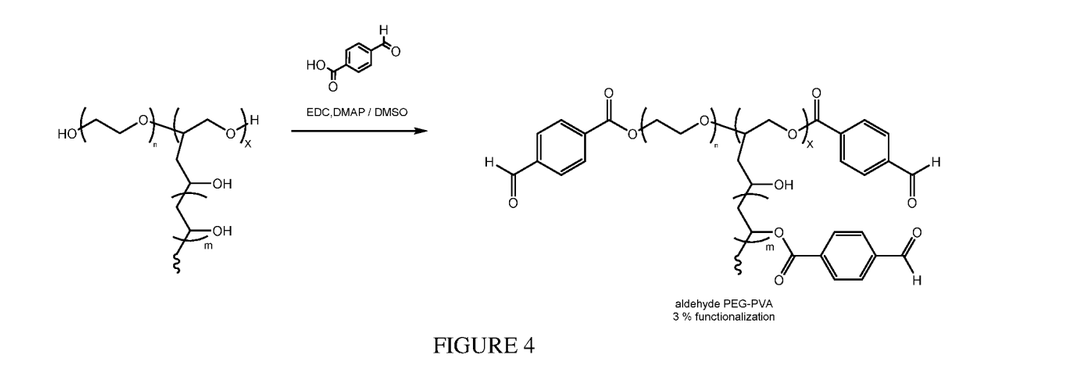
FIG. 4. Synthesis of aldehyde PEG-PVA.

In some embodiments, a PEG-PVA (45,000 g/mole) was esterified with 4-carboxylbenzaldehyde (ald-PEG-PVA) (see FIG. 4). More particularly, PEG-PVA (Kollicoat IR) (3.0 g, 0.066 mmol) was dissolved in anhydrous dimethylsulfoxide (60 mL), followed by addition of 4-carboxybenzaldehyde (1.080 g, 7.2 mmol). The reaction flask was placed into an ice bath followed by addition of N-(3-dimethylaminopropyl)-N'-ethylcarbodiimide hydrochloride (1.380 g, 7.2 mmol) and 4-(dimethylamino)pyridine (39.0 mg, 0.3 mmol). After 48 h methanol (1.5 mL) was added and stirred for 3 h. The crude reaction product was then dialyzed (molecular weight cut off 3,500 g/mole) against methanol to afford the aldehyde PEG-PVA (ald-PEG-PVA) in 3.0% functionalization.

Figure 5A:
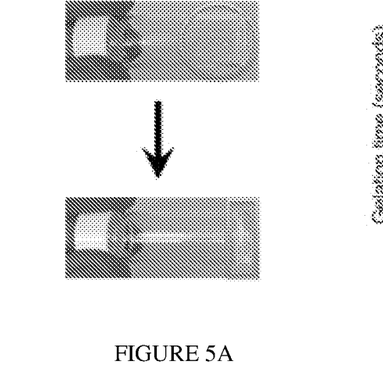
FIG. 5A: upon mixing of ald-PEG and AO-PEG, transparent gels were formed in water at 25° C.
Figure 5B:
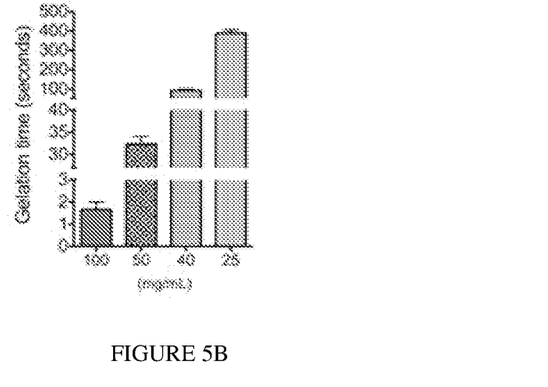
FIG. 5B: tunable gelation times based upon polymer concentration (mg/mL).

In some embodiments, a hydrogel system is provided that was modified by increasing the number of cross-linking sites from four to eight and decreasing the molecular weight to 10,000 g/mole and/or 5,000 g/mole. These modifications increased the weight percent of functional groups, increased the gelation rate, and formed a cross-linked network with minimal swelling. Upon mixing the ald-PEG (10,000 g/mole) and AO-PEG (10,000 g/mole) in deionized water at 25° C. at equal concentrations, transparent hydrogels were rapidly formed (see FIG. 5A). The gelation rate was tunable based upon the weight percent of material from 400 seconds (25 mg/mL) to <2 seconds (100 mg/mL) (see FIG. 5B). Upon mixing the ald-PEG (5,000 g/mole) and AO-PEG (5,000 g/mole) in deionized water at 25° C. at equal concentrations, transparent hydrogels were rapidly formed. The gelation rate was tunable based upon the weight percent of material from 240 seconds (50 mg/mL) to <2 seconds (100 mg/mL) (see FIGS. 15A-D). Upon mixing the ald-PEG-PVA and AO-PEG (10,000 g/mole) in deionized water at 25° C. at equal concentrations, transparent hydrogels were rapidly formed. The gelation rate was tunable based upon the weight percent and was <2 seconds (100 mg/mL) (see FIGS. 15A-D).

Figure 6A:
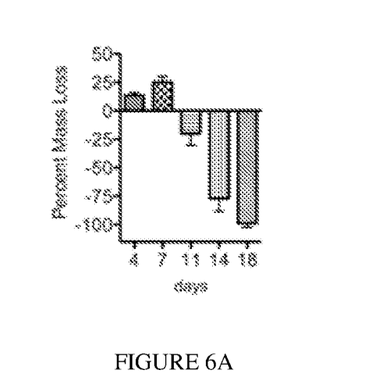
FIG. 6A: percent mass loss over time in PBS at 37° C. for 25 mg/mL gel formulation.
Figure 6B:
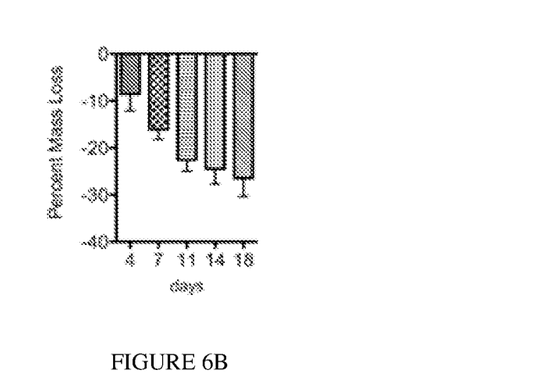
FIG. 6B: percent mass loss over time in PBS at 37° C. for 50 mg/mL gel formulation.

For in vivo applications, the hydrogel is preferably hydrolytically stable for at least two weeks at physiological conditions. The percent mass loss over time was characterized for both the 25 mg/mL and 50 mg/mL hydrogel formulations (see FIGS. 6A-B) that were incubated in 4× the gel volume of PBS, which was changed daily. For the 25 mg/mL gel, an increase in mass percent was observed at one week (likely due to increased swelling) followed by complete loss of the hydrogel after 18 days (see FIG. 6A). However, the 50 mg/mL gel only exhibits a mass loss of 26.5% after 18 days (see FIG. 6B) indicating that at higher concentrations the oxime cross-linked PEG-hydrogel system is hydrolytically stable at physiological conditions past two weeks.

Figure 7:
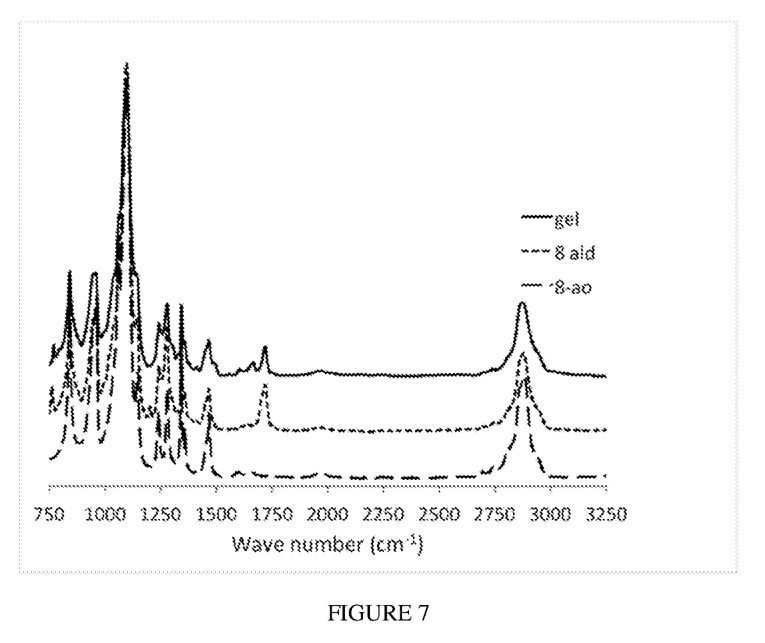
FIG. 7. Infrared spectra of ald-PEG, AO-PEG, and oxime cross-linked hydrogel.

The 100 mg/mL formulation was further characterized since the gelation time was the most rapid for this system. Oxime bond formation was confirmed by infrared spectroscopy from the new peaks between 1600-1750 $cm^{-1}$ for the gel versus the precursor polymers (see FIG. 7). Next, the functional groups ratios were varied from 1:3 to 3:1 aldehyde:aminooxy and it was investigated how excess functional groups affected gelation. These ratios were chosen since larger differences resulted in poor to incomplete gel formation. All three systems 1:1, 1:3, and 3:1 aldehyde:aminooxy gelled immediately upon mixing, which was confirmed by rheometry. All three formulations had similar mechanical properties by parallel plate rheometry with storage moduli (G') at 1 Hz of 750-900 Pa. The gels were highly hydrated with 94.7%, 96.4, and 94.6% water for 1:1, 1:3, and 3:1 hydrogels; respectively. While the 1:1 gel swelled 120% both the 1:3 and 3:1 gels lost 20% of their volume after swelling in PBS for 24 hr. The volume decrease was due to polymer loss during swelling, which was confirmed by mass measurements.

Figure 8A:
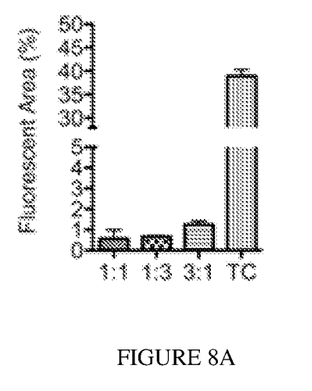
FIGS. 8A-8B. Percent area of fluorescence of membrane labeled (FIG. 8A) 3T3 fibroblasts and (FIG. 8B) RAW macrophages 24 h after seeding (functional group ratio is aldehyde:aminooxy and TC is tissue culture plastic).
Figure 8B:
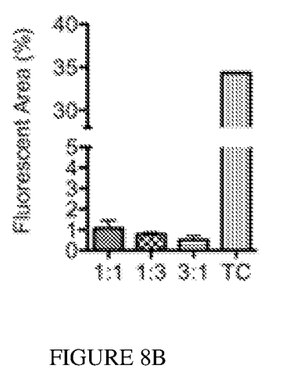

Since functional group ratio affected gel stability it was further tested if an excess of either functional group would change the ability of cells to adhere to the material. The hydrogels were formed and swelled at 37° C. for 24 h. Then 3T3 fibroblasts or RAW macrophages, in which the membrane was fluorescently labeled, were seeded on top of the hydrogels or non-coated tissue culture plastic (TC). These cell types were chosen since they are cell types that infiltrate biomaterials in vivo. The cell volume was optimized to ensure that a monolayer was formed after seeding onto tissue culture plastic (TC), which acted as the positive control. After 24 h, the percent area fluorescence was quantified (see FIGS. 8A-B). Both the fibroblasts (see FIG. 8A) and the macrophages (see FIG. 8B) exhibited less than 2% fluorescent area for all three functional group ratios of the hydrogels, while TC plastic was between 30-40% fluorescent area for both cell types. This demonstrated that excessive amount of either functional group and the oxime bond did not alter the anti-cellular adhesive properties of PEG hydrogels.

Cellular adhesion was observed with the different gel formulations, and it was examined if the elution products exhibited any cytotoxicity by two different methods. First, an agar elution assay was used. A monolayer of cytosol labeled L929 fibroblasts was formed and agar gel containing serum free media was formed over the monolayer. After the cells had been serum starved for 24 h, the three different 100 mg/mL hydrogels (1:1, 1:3, and 3:1 of ald-PEG:AO-PEG) were placed on top of the agar gel and cultured for an additional 24 h. The negative control was a piece of latex and the positive control was a piece of sterile filter paper soaked in serum free media. From bright field images of cells directly beneath the substrates it was observed that there is a distinct difference in cell morphology between the latex and filter paper groups.

Figure 9:
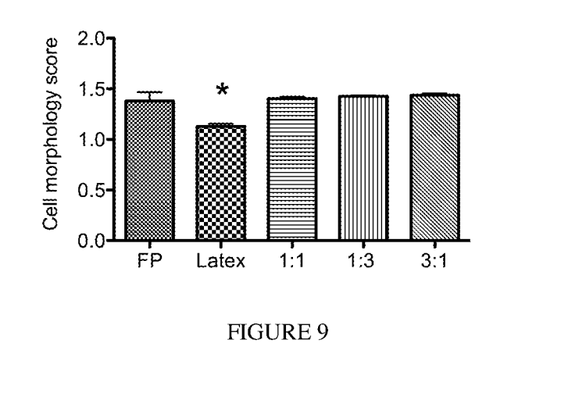
FIG. 9. Results of cytocompatability assay showing fibroblast morphology scores for sterile filter paper soaked in serum free media (positive control), a piece of latex (negative control), and 100 mg/mL hydrogels (1:1, 1:3, and 3:1 of ald-PEG-AO-PEG)

Cells were then scored based upon morphology from 1 to 3. A score of 1 was a rounded cell where the long and short axes were of equal length. A score of 3 was a spread-out cell with multiple protrusions where the long axis was >2 times longer than the short axis. The fibroblasts directly beneath the latex exhibited more rounded morphologies as indicated by the morphology score (see FIG. 9). Fibroblasts directly beneath the hydrogel formulations had similar cell morphology scores to the healthy cells beneath the non-toxic filter paper (see FIG. 9). The lower morphology score for the latex group is indicative of toxic elution products, while the score for the hydrogel groups is similar to the filter paper group.

Figure 10A:
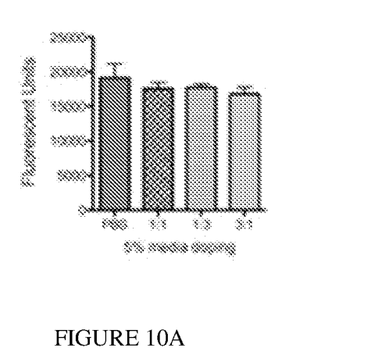
FIGS. 10A-10C. Metabolic activity of 3T3 fibroblasts after 24 h with elution product doped media (functional group ratio is aldehyde:aminooxy and * is $p<0.05$).
Figure 10B:
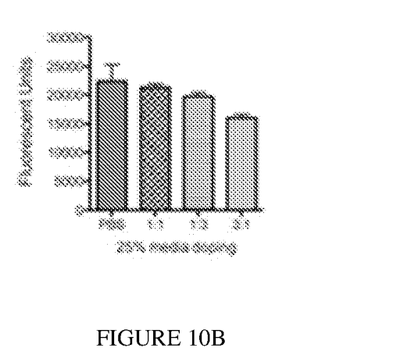
Figure 10C:
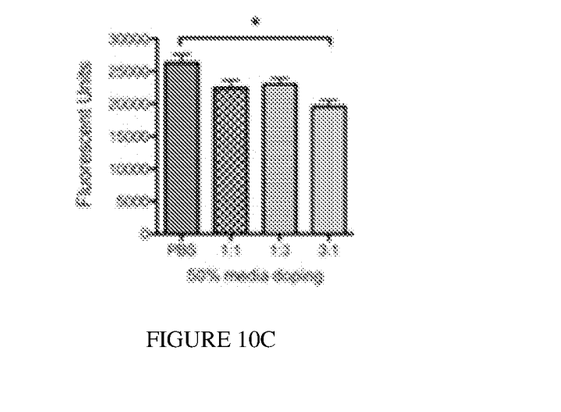

The second cytocompatibilty assay was performed on the elution product using a doped-media assay. A monolayer of 3T3 fibroblasts was serum starved for 24 h. Then the cells were cultured with serum free media doped with different concentrations of elution products from the different hydrogel formulations for 24 h, and the metabolic activity of the cells were measured using Alamar Blue. While all of the 3:1 ald-PEG:AO-PEG doped groups trend lower than the PBS, 1:1, and 1:3 groups show no statistical difference between any of the doped media groups (see FIGS. 10A-C) when compared to media doped with the same amount of PBS. This result combined with the agar elution assay indicate that the elution products of the 1:1, 1:3, and 3:1 ald-PEG: AO-PEG 100 mg/mL hydrogels are cytocompatible.

Finally, the ability to adhere to different cardiac tissue ex vivo was examined. A sodium periodate oxidized dextran/PEG-amine system has been shown to exhibit different adhesion times to different tissues.[16] It was tested if this occurred with oxime cross-linked gels and if excess functional groups altered retention time on different cardiac tissues. Both PEG components were fluorescently labeled. Hydrogels were formed on atrium, ventricle, adipose, and major vessel tissues (aorta and superior vena cava). The elutions from the gels coated tissues were compared to the same volume of gels formed on tissue culture plastic. The PBS was replaced after 1 h, 4 h, 8 h, and then every 24 h for two weeks.

Figure 11:
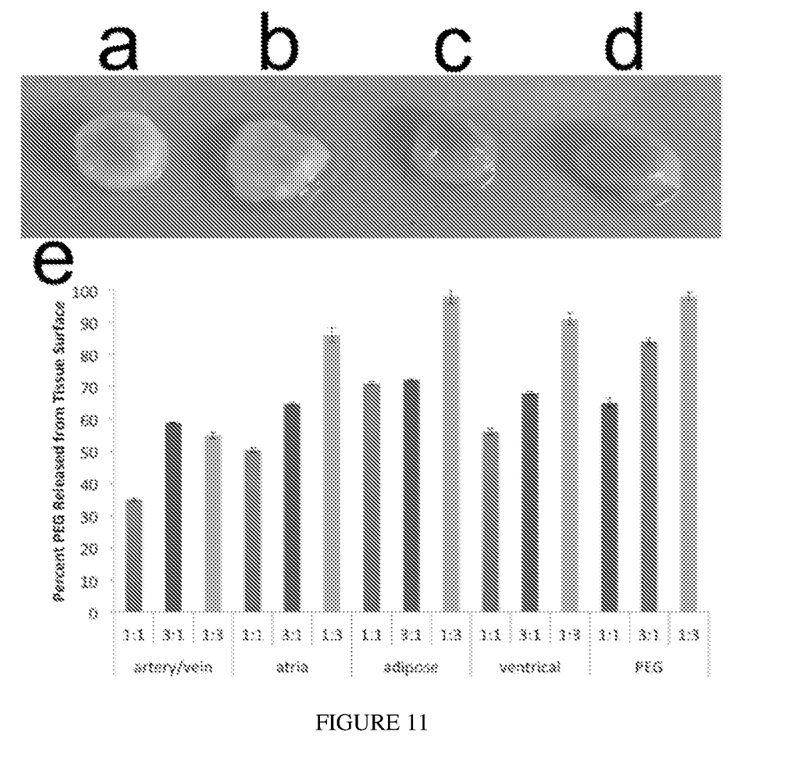
FIG. 11. Tissue sections: (a) vein/artery, (b) adipose (c) atrium and (d) adipose coated with 1:1 aldehyde:amino-oxy after 2 weeks. The graph (e) shows percent PEG released into from tissue surface after two weeks (functional group ratio is aldehyde:amino-oxy).
Figure 12A:
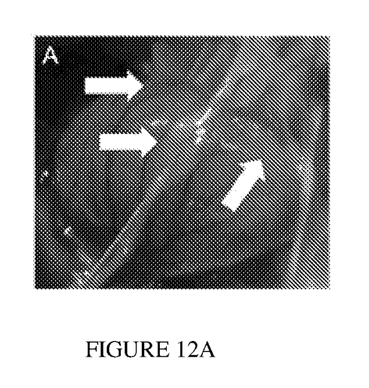
FIGS. 12A-12B. Anterior epicardial surface after cardiac abrasions surgery on rats: no treatment (white arrows mark adhesions on anterior epicardial surface to sternum) (FIG. 12A) and coated with material (presence of material is indicated by shiny clear coating) (FIG. 12B).
Figure 12B:
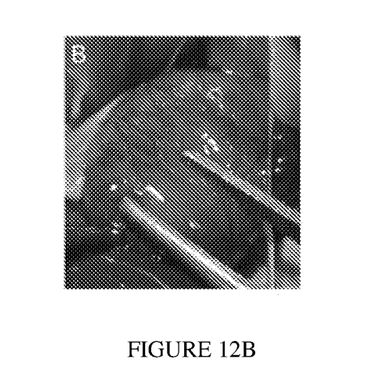
Figure 13A:
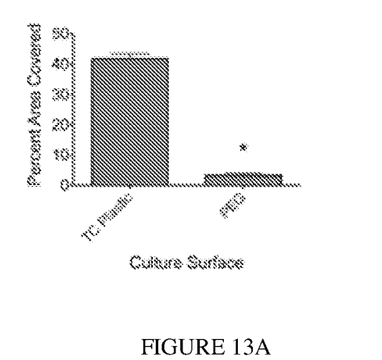
FIG. 13A: Cell morphology assessment of cell directly underneath material; 1.0=rounded, 2.0=ellipsed, and 3.0=stretched out with multiple protrusions ($p<0.001$).
Figure 13B:
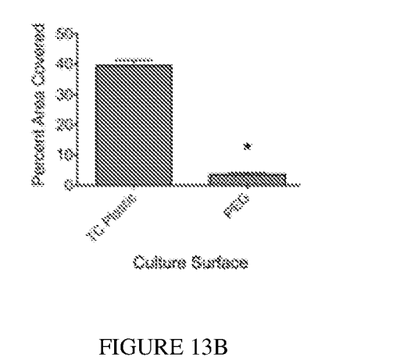
FIG. 13B is the number of cells counted per pictures for morphology assessment. Latex served as a positive control for cytotoxicity.
Figure 14A:
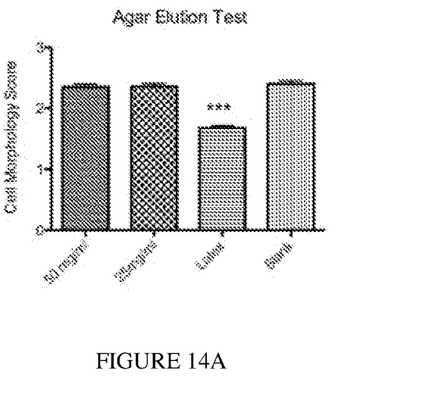
FIGS. 14A-14B. Percent area of fluorescence cover for 3T3 fibroblasts (FIG. 14A) and RAW macrophages (FIG. 14B).
Figure 14B:
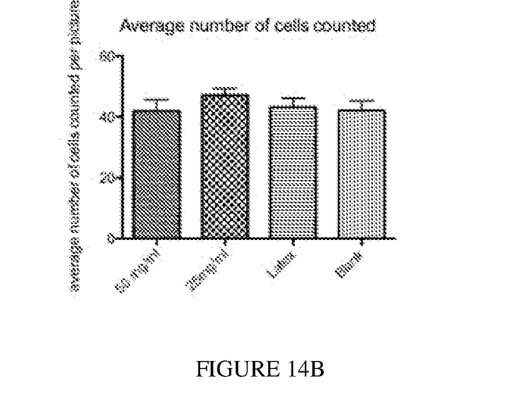
Figure 15A:
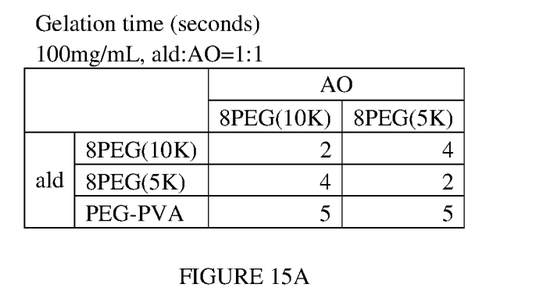
FIG. 15A: each hydrogel has a concentration of 100 mg/mL, ald/AO=1:1.
Figure 15B:
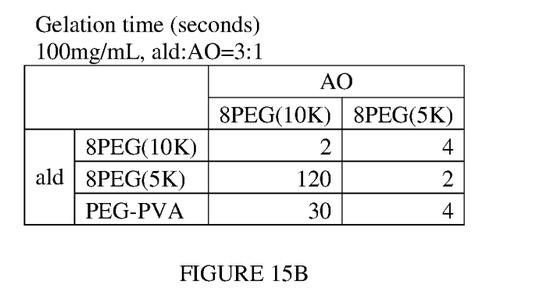
FIG. 15B: each hydrogel has a concentration of 100 mg/mL, ald/AO=3:1.
Figure 15C:
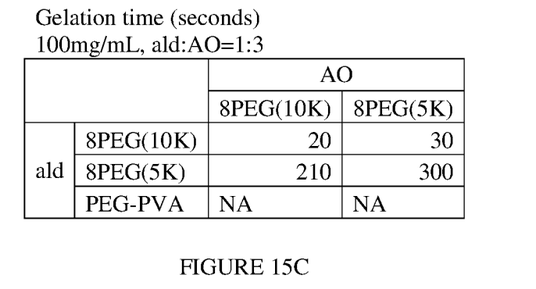
FIG. 15C: each hydrogel has a concentration of 100 mg/mL, ald/AO=1:3.
Figure 15D:
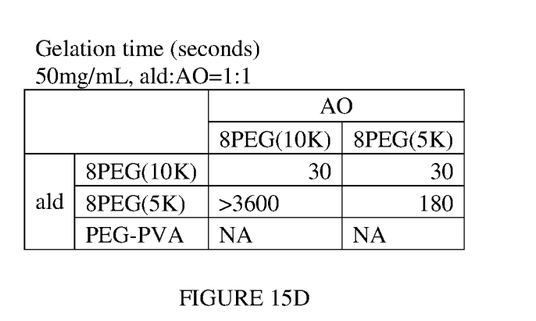
FIG. 15D: each hydrogel has a concentration of 50 mg/mL, ald/AO=1:1.

For all tissues the 1:1 ald-PEG:AO-PEG gels were the slowest degraded with values of 35%, 50%, 71%, 56%, and 65% material loss for major vessels, atrium, adipose, ventricle, and PEG hydrogel; respectively (see FIG. 11, section e), and the gel was still visible on the tissue surfaces (see FIG. 11, sections a-d). The 3:1 ald-PEG:AO-PEG gels had the median amount of material loss over two weeks with 59%, 65%, 72%, 68%, and 84% for major vessels, atrium, adipose, ventricle, and PEG alone; respectively (see FIG. 11, section e). The 1:3 ald-PEG:AO-PEG gels had the highest amount of material loss over two weeks with 55%, 86%, 98%, 91%, and 98% for major vessels, atrium, adipose, ventricle, and PEG alone; respectively (see FIG. 11, section e).

The functional group ratio plays a key role in overall gel stability, and ability to be retained on different tissues after two weeks. The excess of aminooxy groups created the least stable gel and this was generally reflected in the degradation of this formulation on the different cardiac tissues. The excess aldehyde groups would bind to amine residues present on the tissue surface and improve adhesion to tissue and therefore gel stability; however, the 1:1 formulation exhibited the slowest degradation over time once polymerized onto the different cardiac tissues. It is interesting to note that all the materials degrade slower on the vessels and fastest on the adipose tissue, while the muscle tissues (atrium and ventricle) have similar degradation rates. This highlights the balance between functional group ratio, gel stability, and gel reactivity with tissue when designing materials for cardiac applications.

In some embodiments a fast-gelling oxime cross-linked poly(ethylene glycol) (PEG) and/or poly(vinyl alcohol) hydrogel system is provided. The gelation rate and degradation are tunable based upon the weight percent of the polymers. In some embodiments, the gelation rate and degradation rate are tunable based upon the weight percent of the 8-arm aldehyde-PEG and aminooxy-PEG. The 100 mg/mL formulations gel in less than 2 seconds. Variation of the functional group ratio from 1:1, 1:3, and 3:1 ald-PEG: AO-PEG prevent adhesion of fibroblasts and macrophages, and the elution products are cytocompatible. In some embodiments, the cardiac tissue type and the functional group ratio of aldehyde:aminooxy directly impacted the ability of the material to adhere to the different cardiac tissue surfaces. In some embodiments, the type of tissue and functional group ratio effect the rate of gel degradation. In some embodiments, the types of tissue as well as the composition of the gels used to coat the tissue directly impact the retention of the material over time, which has important implications when designing materials for clinical translation.

In some embodiments, the rapid gelling hydrogel for preventing surgical adhesions is a unique system in three aspects: 1) the hydrogel is composed of polymers such as poly(ethylene glycol) (PEG) and/or poly(vinyl alcohol) polymers or copolymers, for example multi-armed PEG components (e.g. PEG-aminooxy and PEG-aldehyde/ketone), that rapidly react to form a hydrogel that can coat tissue surfaces. The formation time of this hydrogel can be tuned from seconds to minutes by polymer concentration or pH of the formulation. This is unique since the three main prior art systems consist of a) thermo-responsive material of hyaluronic acid/cellulose, b) fibrin glue, and c) PEG-NHS+PEG amine/oligo-lysines. The PEG-NHS systems all gel rapidly however, this gelation only occurs over a narrow pH window (pH 7.5-9). In certain embodiments, the oxime cross-linked hydrogels and/or polymer precursors are injectable with a tunable gelation rate of seconds to minutes over a broad range of concentrations (20 mg/mL to 100 mg/mL) and pHs (4-10). This tunability is due to the oxime cross-linking reaction. Furthermore the reactive oxo group (e.g. aldehyde/ketone) component also facilitates adhesion to the tissue surface by reaction with native amines to form imines Additionally, in some embodiments, the oxime cross-linked hydrogels contain hydrolysable ester linkages that can be manipulated to tune the rate of hydrolysis of the material post-gelation; 2) once formed the hydrogel system has very minimal swelling ratio (112%). This is important for application on the heart since material swelling can disrupt the natural function of the organ. This is in direct contrast to the PEG-NHS+amine systems that exhibit a very high swelling ratio from 200-600% of the initial volume; and 3) since the presently disclosed hydrogels are cross-linked via oxime bonds the cross-linking can also be reversed with addition of free aminooxy groups (e.g. hydroxyl amines and alkoxy amines) or free reactive oxo groups (e.g. ketones/aldehydes).

Modifications and variations of the methods and hydrogels described herein will be obvious to those skilled in the art from the foregoing detailed description. Such modifications and variations are intended to come within the scope of the appended claims.

REFERENCES

1. Bouten P J M, Zonjee M, Bender J, Yauw S T K, van Goor H, van Hest J C M, Hoogenboom R. The chemistry of tissue adhesive materials. *Prog Polym Sci.* 2014; 39:1375-1405.

2. Spotnitz W D. Hemostats, sealants, and adhesives: A practical guide for the surgeon. *Am Surgeon.* 2012; 78:1305-1321.
3. Cannata A, Petrella D, Russo C F, Bruschi G, Fratto P, Gambacorta M, Martinelli L. Postsurgical intrapericardial adhesions: Mechanisms of formation and prevention. *Ann Thorac Surg.* 2013; 95:1818-1826.
4. Liakakos T, Thomakos N, Fine P M, Dervenis C, Young R L. Peritoneal adhesions: Etiology, pathophysiology, and clinical significance—recent advances in prevention and management. *Digest Surg.* 2001; 18:260-273.
5. Yeo Y, Kohane D S. Polymers in the prevention of peritoneal adhesions. *Eur J Pharm Biopharm.* 2008; 68:57-66.
6. Nkere U U. Postoperative adhesion formation and the use of adhesion preventing techniques in cardiac and general surgery. *Asaio J.* 2000; 46:654-656.
7. Salminen J T, Mattila I P, Puntila J T, Sairanen H I. Prevention of postoperative pericardial adhesions in children with hypoplastic left heart syndrome. *Interact Cardiov Th.* 2011; 12:270-272.
8. Morales D, Williams E, John R. Is resternotomy in cardiac surgery still a problem? *Interact Cardiov Th.* 2010; 11:277-286.
9. Bel A, Ricci M, Piquet J, Bruneval P, Perier M C, Gagnieu C, Fabiani J N, Menasche P. Prevention of postcardiopulmonary bypass pericardial adhesions by a new resorbable collagen membrane. *Interact Cardiov Th.* 2012; 14:469-473.
10. Leggat P A, Smith D R, Kedjarune U. Surgical applications of cyanoacrylate adhesives: A review of toxicity. *Anz J Surg.* 2007; 77:209-213.
11. Ulrich S, Boturyn D, Marra A, Renaudet O, Dumy P. Oxime ligation: A chemoselective click-type reaction for accessing multifunctional biomolecular constructs. *Chem-Eur J.* 2014; 20:34-41.
12. Ostuni E, Chapman R G, Holmlin R E, Takayama S, Whitesides G M. A survey of structure-property relationships of surfaces that resist the adsorption of protein. *Langmuir.* 2001; 17:5605-5620.
13. Zhang M Q, Desai T, Ferrari M. Proteins and cells on peg immobilized silicon surfaces. *Biomaterials.* 1998; 19:953-960.
14. Grover G N, Lam J, Nguyen T H, Segura T, Maynard H D. Biocompatible hydrogels by oxime click chemistry. *Biomacromolecules.* 2012; 13:3013-3017.
15. Grover G N, Braden R L, Christman K L. Oxime cross-linked injectable hydrogels for catheter delivery. *Adv Mater.* 2013; 25:2937-2942.
16. Artzi N, Shazly T, Baker A B, Bon A, Edelman E R. Aldehyde-amine chemistry enables modulated biosealants with tissue-specific adhesion. *Adv Mater.* 2009; 21:3399.

What is claimed is:

1. A method of protecting internal tissue of an individual with an in-situ post-surgical anti-adhesion barrier, comprising:
   administering to an internal tissue adjacent to a surgical site of an individual in need thereof post-surgery an effective amount of a combination of a first polymer comprising an aminooxy group selected from a hydroxyl amine and an alkoxy amine, and a second polymer comprising a reactive oxo group,
      wherein the first polymer and second polymer are mixed and react to form an oxime cross-linked biocompatible hydrogel proximate to the tissue,
      wherein the oxime cross-linked biocompatible hydrogel forms a protective layer over the tissue to prevent post-surgical tissue adhesions,
      wherein the hydrogel has a surface comprising a surface oxo group, and
      wherein the surface oxo group reversibly binds a surface amine on the tissue to form an imine.

2. The method of claim 1, wherein the tissue is cardiac tissue or another tissue found in the individual's thoracic cavity.

3. The method of claim 1, wherein the oxime cross-linked biocompatible hydrogel is formed in about 5 minutes or less.

4. The method of claim 1, wherein the first polymer and the second polymer are administered by spraying, dripping, or painting the first polymer and the second polymer directly onto the tissue.

5. The method of claim 1, wherein the hydrogel is capable of adhering to the tissue for about two or more weeks.

6. The method of claim 1, wherein the hydrogel reduces cellular adhesion and protein adsorption to the tissue.

7. The method of claim 1, wherein the hydrogel swells to less than about 150% when hydrated.

8. A method of protecting internal tissue of an individual with an in-situ post-surgical anti-adhesion barrier, comprising:
   administering to an internal tissue adjacent to a surgical site of an individual in need thereof post-surgery an effective amount of a combination of a first polymer comprising eight-armed aminooxy poly(ethylene glycol) and a second polymer comprising aldehyde poly(ethylene glycol),
      wherein the first polymer and second polymer are mixed and react to form an oxime cross-linked biocompatible hydrogel proximate to the tissue,
      wherein the oxime cross-linked biocompatible hydrogel forms a protective layer over the tissue to prevent post-surgical tissue adhesions,
      wherein the hydrogel has a surface comprising a surface oxo group, and
      wherein the surface oxo group reversibly binds a surface amine on the tissue to form an imine.

9. The method of claim 8, wherein the tissue is cardiac tissue or another tissue found in the individual's thoracic cavity.

10. The method of claim 8, wherein the oxime cross-linked biocompatible hydrogel is formed in about 5 minutes or less.

11. The method of claim 8, wherein the first polymer and the second polymer are administered by spraying, dripping, or painting the first polymer and the second polymer directly onto the tissue.

12. The method of claim 8, wherein the hydrogel is capable of adhering to the tissue for about two or more weeks.

13. The method of claim 8, wherein the hydrogel reduces cellular adhesion and protein adsorption to the tissue.

14. The method of claim 8, wherein the hydrogel swells to less than about 150% when hydrated.

15. The method of claim 8, wherein the hydrogel comprises approximately between 25 and 200 mg/mL of the first polymer and the second polymer.

16. The method of claim 8, wherein the hydrogel has a storage modulus of about less than 1 kPa.

17. The method of claim 8, wherein the hydrogel swells to less than about 150% by volume when hydrated.

18. The method of claim 1, wherein the reactive oxo group and the surface oxo group are ketones.

19. The method of claim 1, wherein the reactive oxo group and the surface oxo group are aldehydes.

20. The method of claim 1, wherein the aminooxy group is a hydroxyl amine.

21. The method of claim 1, wherein the aminooxy group is an alkoxy amine.

22. The method of claim 1, wherein the first polymer and the second polymer are each selected from the group consisting of poly(ethylene glycol), multi-arm poly(ethylene glycol), hyaluronic acid, alginate, dextran, carboxymethylcellulose, cellulose, poly(vinyl alcohol), or combinations thereof.

23. The method of claim 1, wherein the first polymer comprises eight-armed aminooxy poly(ethylene glycol) and the second polymer comprises aldehyde poly(ethylene glycol).

24. The method of claim 1, wherein the hydrogel comprises approximately between 25 and 200 mg/mL of the first polymer and the second polymer.

25. The method of claim 1, wherein the hydrogel has a storage modulus of about less than 1 kPa.

26. The method of claim 1, wherein the hydrogel swells to less than about 150% by volume when hydrated.

\* \* \* \* \*